United States Patent [19]

Saari et al.

[11] 4,251,530
[45] Feb. 17, 1981

[54] 2-{[4-(6-SUBSTITUTED-2-PYRAZINYL)-1-PIPERAZINYL]ALKYL}-5-SUBSTITUTED-1,2,4-TRIAZOLO[4,3-a]PYRIDIN-3(2H)-ONE ANALGESIC AGENTS

[75] Inventors: Walfred S. Saari, Lansdale; William C. Lumma, Pennsburg, both of Pa.

[73] Assignee: Merck & Co., Inc., Rahway, N.J.

[21] Appl. No.: 122,337

[22] Filed: Feb. 19, 1980

[51] Int. Cl.³ .................. A61K 31/495; C07D 401/14
[52] U.S. Cl. ..................................... 424/250; 544/357; 546/120
[58] Field of Search ........................ 544/357; 424/250

[56] References Cited

U.S. PATENT DOCUMENTS

| | | | |
|---|---|---|---|
| 3,188,313 | 6/1965 | Archer | 544/257 |
| 3,381,009 | 4/1968 | Palazzo et al. | 544/362 |
| 3,917,597 | 11/1975 | Regnier et al. | 544/357 |
| 3,944,551 | 3/1976 | Regnier et al. | 544/357 |
| 4,081,542 | 3/1978 | Lumma et al. | 424/250 |
| 4,082,844 | 4/1978 | Lumma et al. | 424/250 |
| 4,163,849 | 4/1979 | Lumma et al. | 544/357 |

*Primary Examiner*—Donald G. Daus
*Assistant Examiner*—James H. Turnipseed
*Attorney, Agent, or Firm*—Raymond M. Speer; Mario A. Monaco

[57] ABSTRACT

2-{[4-(6-Substituted-2-pyrazinyl)-1-piperazinyl]alkyl}-5-substituted-1,2,4-triazolo[4,3-a]pyridin-3(2H)ones useful as analgesic agents, having the following formula:

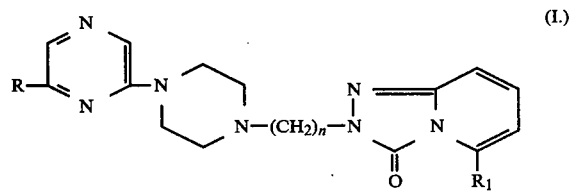

(I.)

wherein p1 n is 2 to 4;
R is halo, methyl, methoxy, or CF$_3$; and
R$_1$ is H or methyl;

and pharmaceutically acceptable salts thereof.

6 Claims, No Drawings

2-{[4-(6-SUBSTITUTED-2-PYRAZINYL)-1-PIPERAZINYL]ALKYL}-5-SUBSTITUTED-1,2,4-TRIAZOLO[4,3a]PYRIDIN-3(2H)-ONE ANALGESIC AGENTS

BACKGROUND OF THE INVENTION

1. Field of the Invention

The present invention is concerned with novel substituted pyrazinylpiperazinyltriazolopyridinones and pharmaceutically acceptable salts thereof which are useful as analgesic agents, to pharmaceutical preparations containing these compounds, and to methods of administering these compounds to an animal or human.

Brief Description of the Prior Art

U.S. Pat. Nos. 4,081,542; 4,082,844; and 4,163,849 all disclose piperazinylpyrazines having serotoninmimetic activity with suggested usefulness as anorexigenic and analgesic agents. U.S. Pat. No. 3,381,009 discloses triazolo-[4,3-a]-pyridines having analgesic activity. However, none of these patents suggests the novel compounds of the present invention and their significantly reduced serotoninmimetic side effects.

SUMMARY OF THE INVENTION

The novel compounds of the present invention have the structural formula:

(I.)

wherein:

n is 2 to 4;

R is halo, i.e., bromo, chloro, or iodo; methyl; methoxy; or trifluoromethyl; and $R_1$ is hydrogen or methyl;

and pharmaceutically acceptable salts thereof.

The most preferred compound of this class is:
2-{3-[4-(6-chloro-2-pyrazinyl)-1-piperazinyl]propyl}-1,2,4-triazolo[4,3-a]pyridin-3(2H)-one.

Also included within the scope of the present invention are non-toxic pharmaceutically acceptable salts. Such acid addition salts of the novel compounds are formed by mixing a solution of the compound with a solution of a pharmaceutically acceptable non-toxic acid such as hydrochloric acid, fumaric acid, maleic acid, succinic acid, acetic acid, citric acid, tartaric acid, sulfuric acid, phosphoric acid, nitric acid, isethionic acid, and the like.

The compounds of the present invention may be prepared by a process in which a N-(6-substituted-2-pyrazinyl) piperazine is reacted with a 5-substituted-2-haloalkyl-1,2,4-triazolo[4,3-a]pyridinone. This reaction may be schematically represented as follows:

where n, R, and $R_1$ are as defined above.

The reaction is carried out either neat, or preferably in an inert solvent, e.g., benzene, toluene, xylene, acetonitrile, ethanol, butanol, dioxane, tetralin, dimethylsulfoxide, or dimethylformamide. It is also desirable to employ a hydrohalic acid acceptor such as a trialkylamine, e.g., triethylamine, or an alkalimetal carbonate such as sodium carbonate. The reaction is carried out at the reflux temperature of the solvent for a period of from 1 to 30 hours.

The 6-substituted pyrazinylpiperazine starting materials may be prepared in accordance with the procedures described in U.S. Pat. No. 4,081,542.

A further embodiment of the present invention is a method of treating pain in patients in need of such treatment that comprises administering to such patients a therapeutically effective amount of a compound of the formula:

(I.)

wherein:

n is 2 to 4;

R is halo, i.e., bromo. chloro, or iodo; methyl; methoxy; or trifluoromethyl; and $R_1$ is hydrogen or methyl;

and pharmaceutically acceptable salts thereof.

In such administration for the treatment of pain, typically the dosage level ranges from about 0.1 to about 300 mg. per day of the active ingredient compounds of the present invention. Thus, pain is effectively treated by the administration of from about 1μg. to 3 mg. of the active ingredient per kilogram of body weight per day. Advantageously, from about 0.1 mg. to 1.0 mg. per kilogram of body weight per daily dosage produces highly effective results.

The amount of active ingredient that may be combined with pharmaceutical carriers to produce a single dosage form will vary depending upon the host treated and the particular mode of administration. For example, a formulation intended for the oral administration of humans may contain from 100 μg. to 20 mg. of active ingredient compounded with an appropriate and convenient amount of carrier material which may vary from about 5 to about 95 percent of the total composition. Dosage unit forms will generally contain between from about 1 mg. to about 10 mg. of active ingredient.

It will be understood, however, that the specific dose level for any particular patient will depend upon a variety of factors including the activity of the specific compound employed, the age, body weight, general health, sex, diet, time of administration, route of administration, rate of excretion, and drug combination.

A still further embodiment of the present invention is a pharmaceutical composition comprising a pharmaceutical carrier and a therapeutically effective amount of a compound of the formula:

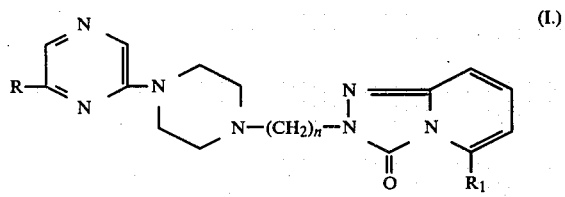

wherein:
n is 2 to 4;
R is halo, i.e., bromo, chloro, or iodo; methyl; methoxy; or trifluoromethyl; and
$R_1$ is hydrogen or methyl;
and pharmaceutically acceptable salts thereof.

The pharmaceutical composition may be in any art recognized form suitable for oral use, such as tablets, troches, lozenges, aqueous or oil suspensions, dispersible powders or granules, emulsions, hard or soft capsules, syrups, or elixers. For intravenous, intramuscular, and subcutaneous use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from about 1 mg. to about 10 mg.

The following examples illustrate the present invention without, however, limiting the same.

EXAMPLE 1

2-{3-[4-(6-chloro-2-pyrazinyl)-1-piperazinyl]propyl}-1,2,4-triazolo[4,3-a]pyridin-3(2H)-one hydrochloride To a solution of 3.2 g. (15.1 mmole) of 2-(3-chloropropyl)-1,2,4-triazolo[4,3-a]pyridin-3(2H)-one in 25 ml. toluene is added 2.4 g. (12.1 mmole) of 6-chloro-2-(1-piperazinyl)pyrazine and 2.1 ml. triethylamine. The mixture is refluxed 3 days under $N_2$, cooled, and filtered to give 1.85 g. of the crude base of the title compound. The crude base is chromatographed on silica gel to give the pure base on elution with 1-2% methanol-chloroform. This material is dissolved in absolute ethanol and the solution treated with anhydrous hydrogen chloride to give tan crystals of title compound, m.p. 243°-245°, dec.

In similar procedures 6-trifluoromethyl-2-(1-piperazinyl)pyrazine gives 2-{3-[4-(6-trifluoromethyl-2-pyrazinyl)-1-piperazinyl]propyl}-1,2,4-triazolo[4,3-a]pyridin-3(2H)-one; 6-methoxy-2-(1-piperazinyl)pyrazine gives 2-{3-[4-(6-methoxy-2-pyrazinyl)-1-piperazinyl]propyl}-1,2,4-triazolo[4,3-a]pyridin-3(2H)-one; and 6-methyl-2-(1-piperazinyl)pyrazine gives 2-{2-[4-(6-methyl-2-pyrazinyl)-1-piperazinyl]-propyl}-1,2,4-triazolo[4,3-a]pyridin-3(2H)-one.

What is claimed is:

1. A compound of the formula:

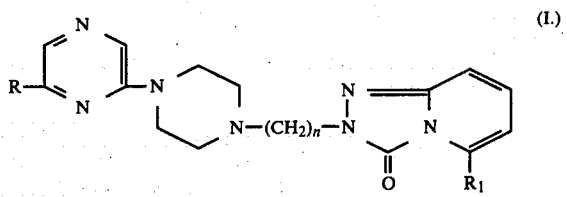

wherein:
n is 2 to 4;
R is bromo, chloro, iodo; methyl; methoxy; or trifluoromethyl; and
$R_1$ is hydrogen or methyl;
and pharmaceutically acceptable salts thereof.

2. A compound as in claim 1 wherein the compound is 2-{3-[4-(6-chloro-2-pyrazinyl)-1-piperazinyl]propyl}-1,2,4-triazolo[4,3-a] pyridin-3(2H)-one.

3. A method of treating pain in a patient in need of such treatment comprising the administration to such a patient of a therapeutically effective amount of a compound of the formula:

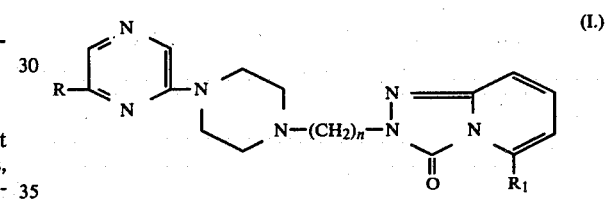

wherein:
n is 2 to 4;
R is bromo, chloro, iodo; methyl; methoxy; or trifluoromethyl; and
$R_1$ is hydrogen or methyl;
and pharmaceutically acceptable salts thereof.

4. A method as in claim 3 wherein the compound is 2-{3-[4-(6-chloro-2-pyrazinyl)-1-piperazinyl]propyl}-1,2,4-triazolo[4,2-a]pyridin-3(2H)-one.

5. A pharmaceutical composition comprising a pharmaceutical carrier and a therapeutically effective amount of a compound of the formula:

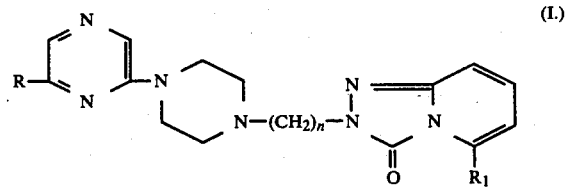

wherein:
n is 2 to 4;
R is bromo, chloro, iodo; methyl; methoxy; or trifluoromethyl; and
$R_1$ is hydrogen or methyl;
and pharmaceutically acceptable salts thereof.

6. A pharmaceutical composition as in claim 5 wherein the compound is 2-{3-[4-(6-chloro-2-pyrazinyl)-1-piperazinyl]propyl}-1,2,4-triazolo[4,2-a]pyridin-3(2H)-one.

* * * * *